United States Patent
Buch-Rasmussen et al.

(10) Patent No.: US 6,582,408 B1
(45) Date of Patent: Jun. 24, 2003

(54) MEDICAL DEVICE

(76) Inventors: Thomas Buch-Rasmussen, Dalvej 28, DK-2820 Gentofte (DK); Benny Munk, Bjæverskov Allé 52, DK-2650 Hvidorre (DK); Jens Ulrik Poulsen, Virumgade 54 C, DK-2830 Virum (DK); Henrik Ljungreen, Jonstrupvej 244A, DK-2750 Ballerup (DK); Peter Møller Jensen, Svenstrupvej 6, D-2970 Hørsholm (DK); Jens Møller Jensen, Nyhavn 37, DK-1051 Copenhagen K (DK)

( * ) Notice: Subject to any disclaimer, the term of this patent is extended or adjusted under 35 U.S.C. 154(b) by 0 days.

(21) Appl. No.: 09/349,748

(22) Filed: Jul. 8, 1999

Related U.S. Application Data

(60) Provisional application No. 60/098,707, filed on Sep. 1, 1998.

(30) Foreign Application Priority Data

Jul. 8, 1998 (DK) .................................. PA 1998 00910
Nov. 17, 1998 (DK) .................................. PA 1998 01501

(51) Int. Cl.[7] .................................................. A61M 5/00
(52) U.S. Cl. ...................................... 604/232; 604/187
(58) Field of Search ............................... 604/186, 187, 604/232, 188, 192, 195, 207–218, 200, 201, 228, 233, 234

(56) References Cited

U.S. PATENT DOCUMENTS

| | | | |
|---|---|---|---|
| 4,744,790 A | 5/1988 | Jankowski et al. | 604/232 |
| 4,865,591 A | * 9/1989 | Sams | 604/186 |
| 4,973,318 A | 11/1990 | Holm et al. | 604/208 |
| 4,990,142 A | 2/1991 | Hoffman et al. | 604/232 |
| 5,364,369 A | * 11/1994 | Reynolds | 604/187 |
| 5,688,251 A | 11/1997 | Chanoch | 604/208 |

FOREIGN PATENT DOCUMENTS

| | | |
|---|---|---|
| EP | 0 702 970 A2 | 3/1996 |
| WO | WO 93/00948 | 1/1993 |
| WO | WO 94/21213 | 9/1994 |
| WO | WO 95/13842 | 5/1995 |
| WO | 0 688 571 A1 | 12/1995 |
| WO | WO 96/02290 | 2/1996 |
| WO | WO 97/49620 | 12/1997 |
| WO | WO 99/16487 | 4/1999 |

OTHER PUBLICATIONS

Abstract of Australian patent application AU–A–73 632/81.

* cited by examiner

*Primary Examiner*—Brian L. Casler
*Assistant Examiner*—Kevin C. Sirmons
(74) *Attorney, Agent, or Firm*—Marc A. Began, Esq.; Richard W. Bork, Esq.; Reza Green, Esq.

(57) ABSTRACT

The present invention relates to a medication delivery device comprising a cartridge assembly, a dosing assembly and optionally a needle assembly. The cartridge assembly comprises a cartridge having a stopper adapted to receive a plunger. Furthermore, the cartridge assembly has one end sealed with a pierce able sealing, said end comprising coupling device for engaging a needle assembly, and another end comprising coupling device for engaging the dosing assembly. The dosing assembly comprises a plunger and has coupling device for engaging the cartridge assembly. The cartridge assembly and the dosing assembly are coupled together for delivering selected doses of medication. The device further comprises mechanism for securing that the plunger abuts on the stopper during use of the device, in particular when the dosing assembly is releasable coupled to the cartridge assembly. The securing mechanism is preferably a mechanism for preventing the cartridge assembly from being inadvertently released from the dosing assembly. The cartridge is preferably molded from a plastic material, such as a transparent material, and may be housed in a cartridge housing for protection of the cartridge. The medication delivery device is especially suitable for delivering insulin, growth hormone or the like medicines.

11 Claims, 2 Drawing Sheets

MEDICAL DEVICE

CROSS-REFERENCE TO RELATED APPLICATIONS

This application claims priority under 35 U.S.C. 119 of Danish application serial nos. PA 1998 00910 filed Jul. 8, 1998, PA 1998 01501 filed Nov. 17, 1998, and U.S. Provisonal application serial No. 60/098,707 filed Sep. 1, 1998, the contents of which are fully incorporated herein by reference.

BACKGROUND

Some medication, such as insulin is self-administered. The typical diabetes patient will require injections of insulin several times during the day. The required insulin dose will vary from patient to patient, and will for each patient often also vary during the day. Each patient will often establish a regimen for the insulin administration adjusted to his or her insulin need as well as lifestyle. Medication delivery pens have been developed to facilitate the self-administration of medication, such as insulin.

One prior art medication delivery pen includes a pen body assembly comprising a medication cartridge and a plunger device. A needle assembly may be connected to the pen body assembly. The medication is delivered by moving or pressing a plunger in the direction of the needle assembly, thereby delivering the medication. When the medication in the cartridge is exhausted, the pen body assembly is discarded. Depending on the medication needs for each individual the medication in the cartridge will last for several days. During this period the needle assembly will often have to be replaced by a new assembly or new needle due to increasing bluntness of the needle making injections painful for the patient.

Due to the environmental and economical reasons medication delivery pens were developed, for which pens only a part of the pen was discarded after medication exhaustion, such as the cartridge only.

An example of prior art pens is disclosed in EP 0 688 571 wherein a medication delivery pen has a reusable pen body assembly and a disposable cartridge assembly that are threadedly engageable with one another. The disposable cartridge assembly includes a plunger and can releasable receive a needle cannula assembly through a threaded coupling. A driving means in the pen body assembly engages the plunger after engagement of the pen body assembly and the cartridge assembly, whereby the pen is ready for dosing the medicine within the cartridge. The cartridge holder assembly can be disassembled from the pen body assembly after the medication therein has been exhausted, discarded and replaced.

However, a drawback of the above-mentioned pen is that the driving means of the pen body may be disengaged from the plunger of the cartridge during normal use resulting in inaccurate dosing of the medicine.

For the device disclosed in EP 0 688 571, the needle assembly will often have to be replaced independently of replacement of the cartridge. When releasing the needle assembly from the cartridge assembly the cartridge assembly may inadvertently be released or partly released from the pen body assembly. Thereby the driving means of the pen body may be disengaged from the plunger of the cartridge. In particular if the pen body assembly is only partly released from the cartridge assembly the user will most probably not be aware of the disengagement but will receive only a portion or even nothing of the medicine.

Even pens with differently pitched threaded couplings and/or threaded couplings having different diameters whereby the force exerted to fasten and/or release one coupling is greater than the force necessary for the other coupling present this problem. It is easy to imagine that a small obstruction (a sandskorn, for example) to the smoothest going coupling will necessitate a greater force to fasten/release that coupling which force tends towards the force necessary for the other coupling.

Accordingly, it is an object of the present invention to provide a medication delivery device with which the inadvertent disengagement of the driving means and plunger means from the plunger or stopper in the cartridge is avoided.

SUMMARY OF THE INVENTION

According to a first aspect of the invention a medication delivery device is provided which comprises a cartridge assembly, having one end sealed with a pierce able sealing, said end of the cartridge assembly comprising coupling means for releasable mounting a needle assembly, and comprising a cartridge having a stopper adapted to receive plunger means, a dosing assembly comprising plunger means, and optionally a needle assembly, wherein the cartridge assembly and the dosing assembly are coupled together, and the device further comprises means for securing that the plunger means abuts on the stopper during use of the device.

In a preferred embodiment the dosing assembly is reusable and the cartridge assembly is disposable, and accordingly, a second aspect of the present invention is a medication delivery device wherein the dosing assembly is releasable coupled to the cartridge assembly.

By the term "use of the device" is meant the normal use, including metering and delivering the medication, removing a cap from the cartridge assembly and/or needle as well as attaching and releasing the needle assembly. It is understood that the plunger means must disengage the stopper when the cartridge assembly is deliberately released from the dosing assembly because the medication in the cartridge has been exhausted and the cartridge assembly is to be discarded. In this situation the plunger means is to be retracted to the dosing assembly before assembling the device with a new cartridge assembly.

Securing the abutment of the plunger means on the stopper during use of the medication delivery device, in particular when the needle assembly is coupled to and/or decoupled from the cartridge assembly, may be carried out by a variety of means. In a preferred embodiment the abutment is secured by preventing the cartridge assembly from being inadvertently released from the dosing assembly.

Furthermore, it is a preferred aspect of the invention to provide a medication delivery device, which device is arranged for securing that the plunger means abuts on the stopper during coupling and/or decoupling of the needle assembly.

In one embodiment of the invention the dosing assembly is coupled to the cartridge assembly at the end of the cartridge assembly opposite the means for mounting the needle assembly, and the plunger means is a rod element adapted to exert an axial movement of the stopper towards the sealed end of the cartridge.

Accordingly, it is an aspect of the present invention to provide a medication delivery device, wherein the means for coupling the dosing assembly and the cartridge assembly together are such that the coupling and/or decoupling of the needle assembly does not cause an axial movement of the cartridge assembly with respect to the dosing assembly. In this way it is assured that the rod element does not disengage the stopper in the cartridge when the user attaches the needle assembly or removes it after use. Thereby the user can be confident of the accuracy of the dosage selected.

The means for coupling the dosing assembly and the cartridge assembly together may be any suitable coupling, preferably a releasable coupling. Examples of the coupling are snap locks, such as snap locks with guidewire and sideways snap locks, snap locks released through threads, bajonet locks, luer locks, hinged locks, threaded locks and any suitable combinations thereof.

In particular, when the cartridge assembly is released from the dosing assembly through a movement including an axial movement, such as through a threaded coupling, it is preferred that the means for releasable coupling the needle assembly and the cartridge assembly together are such that the coupling and/or decoupling of the needle assembly cannot cause an axial movement of the cartridge assembly with respect to the dosing assembly. Thus, in that respect examples of the preferred couplings between the needle assembly and the cartridge assembly include releasable snap locks. Another preferred embodiment includes a safety on the coupling between the dosing assembly and the cartridge assembly, such as hinge on the coupling or a threaded coupling releasable only after exerting an axial pressure on the coupling.

According to the invention preferred combinations of couplings between the dosing assembly and the cartridge assembly and between the needle assembly and the cartridge assembly, respectively, are a threaded coupling combined with a snap coupling, a bajonet lock or a luer lock combined with a snap lock, or a snap lock combined with a snap lock, or any other combination for which the couplings are independently working.

Another aspect of the present invention is a cartridge assembly for use in the medication delivery device according to the invention. The cartridge assembly comprises a cartridge for the medication to be delivered. The cartridge assembly has one end sealed with a pierce able sealing, said end of the cartridge assembly comprising coupling means for releasable mounting a needle assembly, and another end comprising coupling means adapted to engage a dosing assembly. Furthermore, the cartridge comprises a stopper.

The cartridge assembly may further comprise a housing for protecting at least a part of the cartridge assembly.

In a preferred embodiment at least one of the coupling means of the cartridge assembly is unitarily molded with the cartridge, and in a more preferred embodiment all the coupling means are unitarily molded with the cartridge. In the latter case the cartridge assembly may be comprised of just one part, i.e. the cartridge including the coupling means.

In another embodiment the invention relates to a medication delivery device for transferring medication from the cartridge into a syringe with a needle. In this embodiment the coupling means for engaging the needle assembly may be replaced by coupling means for engaging the syringe, or coupling means for both may be provided. The coupling means may be a syringe holder, for example a cylinder coupled to the cartridge comprising a central bore for receiving the syringe. The syringe is coupled to the cartridge having the needle piercing the sealing. By activation of the dosing means the metered amount of medication is driven into the syringe. The syringe is then ready for injection after being removed from the cartridge.

DRAWINGS

DETAILED DESCRIPTION OF THE INVENTION

Figure 1:
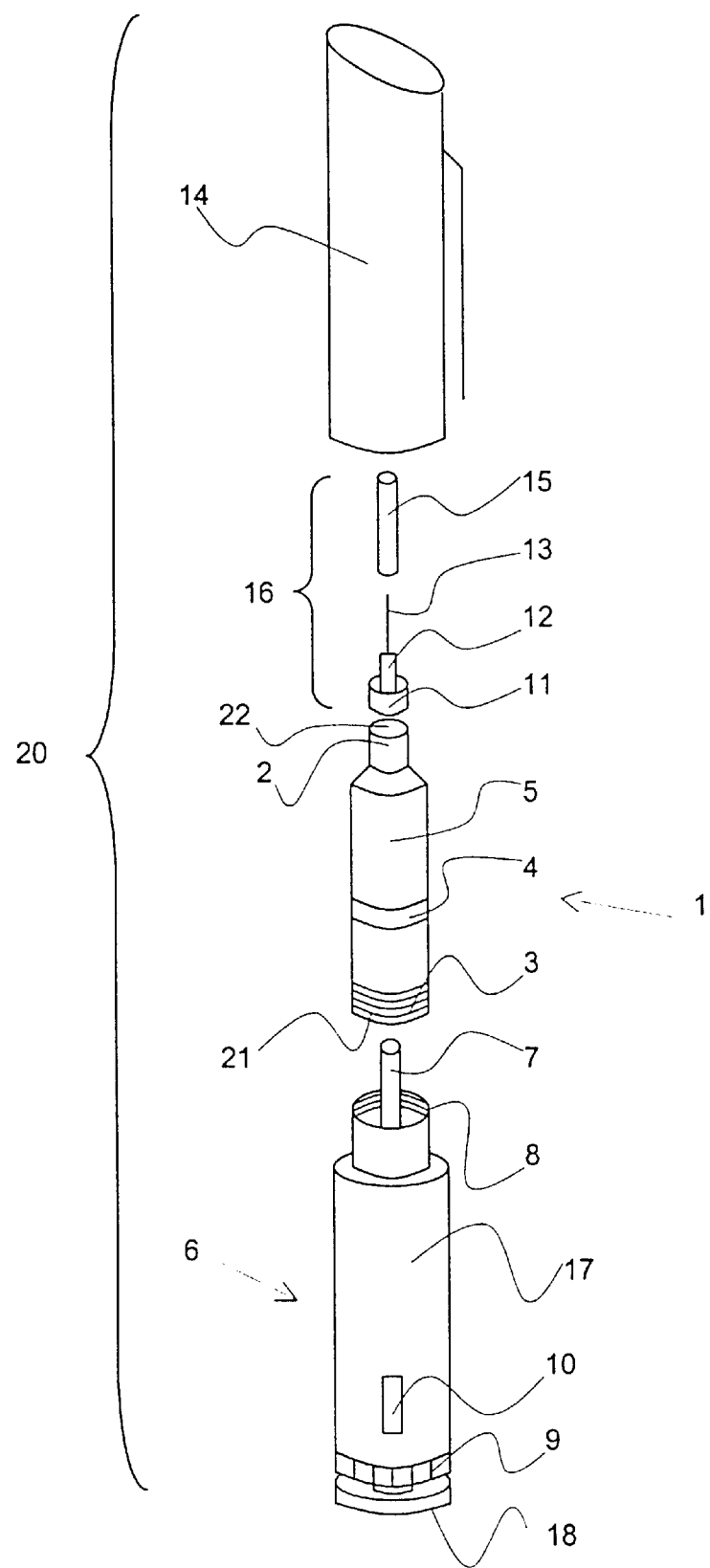
FIG. 1 is an exploded perspective view of the medication delivery device.
Figure 2A:
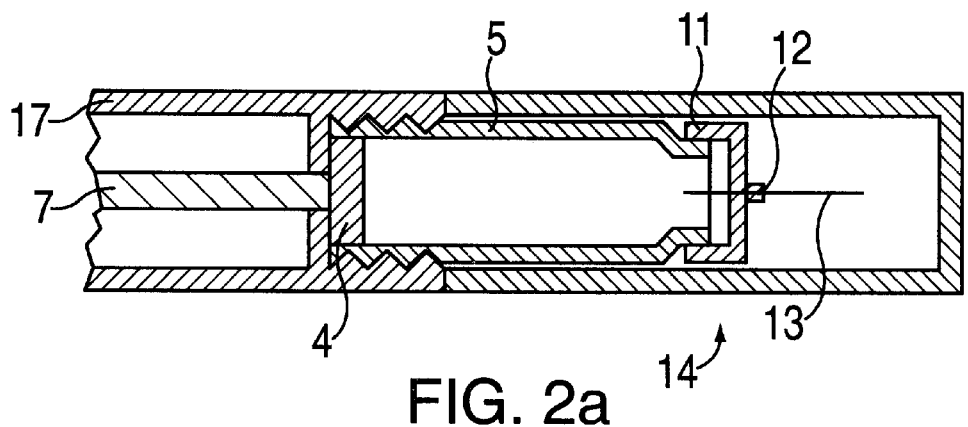
FIG. 2 is a cross-sectional view showing part of the medication delivery device, 2a immediately after assembling before the first injection, and 2b after some time of use.
Figure 2B:
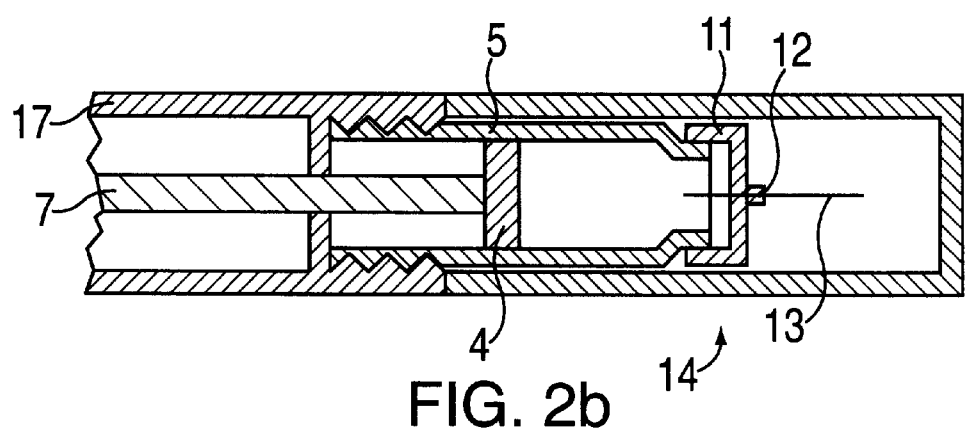

A medication delivery device in accordance with the present invention is identified generally by the numeral 20 in FIG. 1 and 2. Medication delivery device 20 includes a dosing assembly 6, and cartridge assembly 1, a needle assembly 16 and a cap 14.

The dosing assembly 6 is illustrated in FIGS. 1 and 2. It is understood, however, that the dosing assembly 6 according to the invention may be any suitable dosing unit including plunger means and, accordingly, that variations from the depicted embodiment may be provided, and are considered to be within the scope of this invention. In the depicted embodiment, the dosing assembly 6 includes a cylindrical housing 17 surrounding the plunger means of the dosing unit and having opposed proximal and distal ends.

In one aspect of the invention the plunger means comprises a rod element 7 which is adapted to engage the stopper 4 of the cartridge assembly 1. The rod element 7 advances axially into the cartridge 5 during injections. The dosing assembly may have any suitable driving means for advancing the rod element 7.

The dosing unit 6 preferably also comprises scale means 10 indicating the dosing quantity selected by activating the dose setting means 9 for defining specified selected doses of medication to be delivered. The selected dose may be delivered by actuating the actuator button 18. The actuator button is part of the driving means of the dosing assembly exerting its force on the rod element 7.

The dosing assembly further comprises coupling means 8 adapted for engagement with the cartridge assembly. The coupling means 8 may be internal or external couplings. In a preferred embodiment the coupling 8 is an internal coupling.

Figure 3:
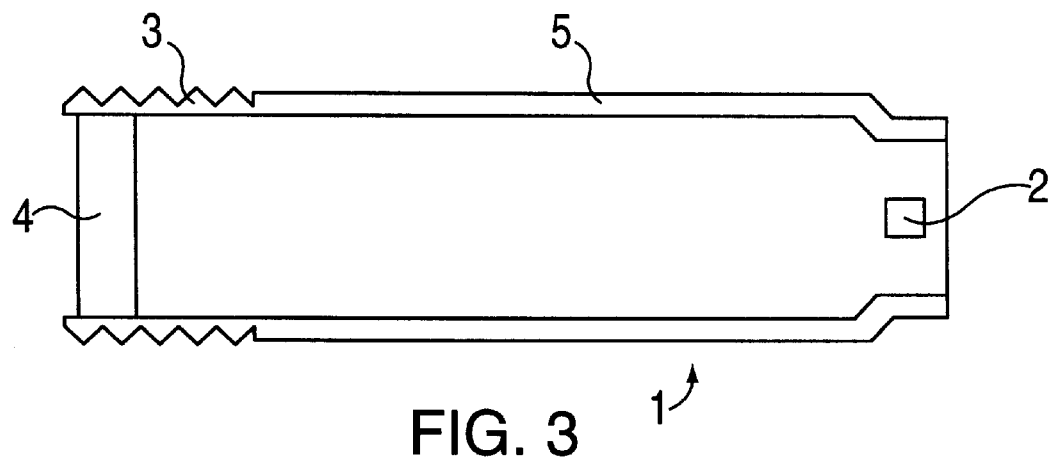
FIG. 3 is a cross-sectional view showing the cartridge before assembling of the medication delivery device.

The cartridge assembly 1 is illustrated in FIGS. 1 and 2, and in greater detail in FIG. 3. In FIG. 1 cartridge assembly 1 includes a molded cartridge 5 extending from proximal end 21 to distal end 22.

At the distal end 22 of the cartridge assembly 1 is provided coupling means 2 for releasable mounting a needle assembly 11. At the proximal end 21 of the cartridge assembly 1 is provided coupling means 3 for mounting a dosing assembly 6. The coupling means are as described above.

Cartridge 5 also comprises a stopper 4 in sliding fluid tight engagement within said cartridge 5. The stopper 4 is adapted to receive the plunger means, such as a rod element 7 of the dosing assembly 6.

The cartridge assembly 1 may further comprise a housing for protecting some or all of the cartridge 5. When the cartridge assembly 1 includes a housing, one or both of the couplings 2, 3 of the cartridge may be molded unitarily with the housing.

In a preferred embodiment at least one of the couplings 2, 3 is molded unitarily with the cartridge 5, minimising the total number of parts of the device and thereby the production costs. Also, a very precise coupling is obtained, since no further steps are to be taken to attach the coupling means to the catridge.

Instead of the protective housing the cartridge 5 may have integrally molded reinforcements of the cartridge wall.

The depicted cartridge 5 is cylindrical having couplings 2, 3 at opposed ends. However, the cartridge may obtain any suitable form and the cross-section may be circular or non-circular, such as substantially triangular or oval.

In FIG. 1 and FIG. 2 the couplings 2, 3 are opposing each other having the same axis. However, the axis of coupling 2 may be arranged to be separate from coupling 3, that is in any angle with respect to the axis of coupling 3. Thus, the axis of coupling 2 may be perpendicular to the axis of coupling 3, or they may be parallel but not overlapping.

A suitable choice of material allows the cartridge to be at least partly transparent, whereby the user can see whether any content, such as a liquid is left in the cartridge.

Referring to FIG. 3 the coupling means of the cartridge are shown in greater detail. The coupling means 3 is an external thread, whereas the coupling means 2 is a recess for a snap lock of the needle assembly. Both coupling means are molded unitarily with the cartridge.

The device according to the invention may include a protective cap 14 that is removably mounted over the cartridge assembly 1 and/or the needle 11 and which is removed before injection of the medication in the cartridge 5. The cap further ensures that the content of the cartridge is protected against sunlight.

The various parts of the medication delivery device are advantageously made of plastics, e.g. by injection moulding.

The medication delivery device 20 may further comprise any appropriate needle assembly 11, such as a double ended needle 13 having opposed proximal and distal points and a lumen extending axially therebetween.

A mounting hub 12 is engaged on the needle 13 and is removably connected to the coupling means 2 at the needle end of the cartridge assembly. The relative location of the mounting hub 12 ensures that the proximal point of the needle 13 will pierce the sealing when the mounting hub 12 is engaged with the coupling means 2 on the cartridge assembly 1.

The needle assembly 11 may further comprise a removable shield or cap 15 for protecting against accidental needle sticks.

The device according to the invention is suitable for delivering pre-set dosages of insulin, it is however understood that the device is suitable for the injection of pre-set dosages of other liquids.

In use the user will set the dose by means of the dose setting means 9. Before activating the actuator button 18 the cap 14 must be removed from the cartridge assembly 1 whereby the device 20 is prepared for an injection. The injection is effected by activating the actuator button 18, which again will effect the stopper 4 to be moved towards the needle at the sealed end 22 of the cartridge 5, thereby delivering the desired pre-set dosage. A subsequent dosage of medication will be set in exactly the same manner as described above. However, for such a subsequent dosage, the rod element 7 and the stopper 4 will be in a partly advanced position as starting point. Dose setting and injections can be carried out until all of the medication has been used.

What is claimed is:

1. A medication delivery device comprising:
   a cartridge assembly comprising a cartridge having a pierceable seal at one end and a moveable stopper at an opposite end;
   a dosage assembly comprising a plunger means for acting on the stopper; a mechanism for setting a specified dose; and a drive means for advancing the plunger means to deliver the specified dose;
   a needle assembly;
   a first coupling means for coupling and uncoupling the needle assembly to and from the cartridge assembly;
   a second coupling means for coupling and uncoupling the cartridge assembly to and from the dosage assembly;
   wherein the first coupling means comprises a snap lock; and
   wherein the second coupling means is selected such that when a user grasps the needle assembly and applies a force to couple it to and to uncouple it from the cartridge assembly, while simultaneously grasping the dosage assembly and applying an equal but opposite force thereto, the cartridge assembly cannot not move axially with respect to the dosage assembly.

2. The medication delivery device of claim 1, wherein the first coupling means comprises a means for coupling or uncoupling the needle assembly through an axial movement of the needle assembly relative to the cartridge assembly and the second means comprises a threaded means.

3. The medication delivery device of claim 2, wherein the cartridge assembly comprises a housing for receiving the cartridge and wherein the snap lock is an integral part of the needle assembly.

4. A medication delivery device upon which a needle assembly can be mounted, the device comprising:
   a cartridge assembly comprising a cartridge having a movable stopper at one end and a pierceable seal at an opposite end;
   a dosage assembly comprising a mechanism for setting a specified dose, a plunger means for abutting the moveable stopper, and a drive means for driving the plunger means to deliver the set doseage;
   a first coupling means for coupling and uncoupling the cartridge assembly to and from the dosage assembly; and
   a second coupling means for coupling and uncoupling a needle assembly to and from the cartridge assembly;
   wherein the first and second coupling means are selected so that when a user grasps the needle assembly and applies force to the needle assembly to couple and uncouple it from the device while simultaneously grasping the dosage assembly and applying a equal and opposite force to the dosage assembly, the dosage assembly cannot move relative to the cartridge assembly, thereby ensuring that the plunger means remains abutted against the stopper; and
   wherein the first or second coupling means comprises a snap lock.

5. The medication delivery device recited in claim 4, wherein the second coupling means comprises a threaded coupling means and wherein the second coupling means comprises a means for coupling and uncoupling through an axial movement of the needle assembly relative to the cartridge assembly.

6. The medication delivery device of claim 4, wherein the first coupling means comprises a means for uncoupling through an axial movement of the cartridge assembly relative to the dosing assembly.

7. The medication delivery device of claim 4, wherein the first coupling means comprises a threaded coupling means.

8. The medication delivery device of claim 4, wherein the cartridge assembly comprises a housing to accommodate the cartridge and wherein the second coupling means comprises a means for axially coupling or uncoupling the needle assembly from the cartridge assembly.

9. The medication delivery device of claim 4, wherein the second coupling means comprises a threaded coupling means.

10. A medication delivery device comprising:

a cartridge assembly comprising:
  a housing capable of housing a removable cartridge that has a pierceable seal at one end, is filled with medication, and has a moveable stopper at an opposite end that when moved toward the medication pressurizes the medication; and
  a needle mounting means for mounting a needle on the cartridge assembly;

a dosage assembly for delivering a set dose of medication, comprising:
  a plunger means for moving the stopper, a dose setting means for setting a dose, and a drive means for driving the plunger means to deliver the set dose, wherein after a portion of medication is expelled from the cartridge, the plunger means abuts the stopper;

a first means for coupling and uncoupling a needle assembly to and from the cartridge assembly;

a second means for coupling and uncoupling the dosage assembly to and from the cartridge assembly;

wherein the first and second coupling means are chosen so that when a user simultaneously grasps the dosage assembly and the needle assembly and applies a force to the needle assembly to couple (or uncouple) the needle to or from the device the cartridge assembly is positively precluded from moving axially relative to the cartridge assembly; and wherein at least the first or the second coupling means comprises a snap lock.

11. A medication delivery device comprising:

a cartridge assembly for housing a removable cartridge containing a medication;

a needle assembly;

a dosage assembly comprising a mechanism for setting a dosage less than the full amount of medication contained in the cartridge;

a first coupling means for coupling and uncoupling the needle to and from a removable cartridge housed in the cartridge assembly; and a second coupling means for coupling and uncoupling the cartridge assembly to and from the dosage assembly;

wherein the first coupling means comprises a snap lock; and wherein the second coupling means is chosen so that when a user couples or uncouples the needle assembly from the cartridge by grasping the needle assembly and the dosage assembly simultaneously and applying force to both, the second coupling means prevents axial movement of the cartridge assembly relative to the dosage assembly.

* * * * *

UNITED STATES PATENT AND TRADEMARK OFFICE
CERTIFICATE OF CORRECTION

PATENT NO. : 6,582,408 B1
DATED : June 24, 2003
INVENTOR(S) : Buch-Rasmussen et al.

It is certified that error appears in the above-identified patent and that said Letters Patent is hereby corrected as shown below:

Column 6,
Line 23, "cannot not move" should read -- cannot move --.

Column 8,
Line 7, "cartridge assembly" should read -- dosage assembly --.

Signed and Sealed this

Thirteenth Day of September, 2005

JON W. DUDAS
*Director of the United States Patent and Trademark Office*